(12) United States Patent  
Roger-Dalbert

(10) Patent No.: US 7,235,379 B2
(45) Date of Patent: Jun. 26, 2007

(54) METHOD AND MEDIUM FOR THE DETECTION/IDENTIFICATION OF MICROORGRANISMS WITH ESTERASE ACTIVITY

(75) Inventor: Céline Roger-Dalbert, Vaux-En-Bugey (FR)

(73) Assignee: Bio Merieux, Marcy l'Etoile (FR)

( * ) Notice: Subject to any disclaimer, the term of this patent is extended or adjusted under 35 U.S.C. 154(b) by 427 days.

(21) Appl. No.: 10/416,298

(22) PCT Filed: Nov. 16, 2001

(86) PCT No.: PCT/FR01/03610

§ 371 (c)(1),
(2), (4) Date: Jun. 6, 2003

(87) PCT Pub. No.: WO02/40704

PCT Pub. Date: May 23, 2002

(65) Prior Publication Data

US 2004/0048326 A1  Mar. 11, 2004

(30) Foreign Application Priority Data

Nov. 17, 2000 (FR) .................................. 00 14881

(51) Int. Cl.
*C12Q 1/04* (2006.01)
(52) U.S. Cl. ..................................................... 435/34
(58) Field of Classification Search ................. None
See application file for complete search history.

(56) References Cited

FOREIGN PATENT DOCUMENTS

| | | | |
|---|---|---|---|
| FR | 2 697 028 | | 4/1994 |
| WO | 92/17607 | * | 10/1992 |
| WO | WO 92/17607 | | 10/1992 |
| WO | WO 94/09152 | | 4/1994 |
| WO | WO 99/41409 | | 8/1999 |

OTHER PUBLICATIONS

Cooke et al., "A Novel Chromogenic Ester Agar Medium for Detection of *Salmonellae*", *Applied and Environmental Microbiology*, vol. 65, No. 2, Feb. 1999, pp. 807-812.
International Search Report PCT/FR01/03610 dated Mar. 1, 2002.

* cited by examiner

*Primary Examiner*—Sandra E. Saucier
(74) *Attorney, Agent, or Firm*—McCracken & Frank LLP

(57) ABSTRACT

The invention relates to a method and a medium for microbiological analysis by biochemical means involving chromogenic or fluorogenic substrates that react with enzymes (esterases) specific for the target strains.

One object of the invention is to improve the sensitivity, initial translucence, stability and ease of use of such detection/identification media. For this purpose the medium according to the invention is characterized in that it is in a stable, ready-to-use liquid or gel form and in that it contains a solubilizer and stabilizer selected from fatty acid sorbitan esters, bile salts and mixtures thereof, as well as a selective activator selected from alkylsulfate salts, for example the sodium salts. The medium can comprise a solvent, for example dimethyl sulfoxide.

The invention further relates to the method of obtaining this medium and to the use of products of the sodium alkylsulfate type as selective activators in such media.

Application: microbiological analyses.

32 Claims, No Drawings

METHOD AND MEDIUM FOR THE DETECTION/IDENTIFICATION OF MICROORGRANISMS WITH ESTERASE ACTIVITY

This application is a U.S. National Stage of International application PCT/FR01/03610, filed on Nov. 16, 2001

The field of the invention is that of microbiological analysis by biochemical means and in particular the detection and identification of strains of microorganisms by the inoculation of reaction media, particularly nutrient media. The latter comprise chromogenic or fluorogenic substrates that are capable of reacting with enzymes specific for the target strains to produce a coloration or a fluorescence for each colony in question.

Of more particular interest within the framework of the present disclosure is the detection/identification of microorganisms with esterase activity and more especially bacteria of the genus *Salmonella*.

This genus *Salmonella* is the most important genus of the family Enterobacteriaceae, which are responsible for a variety of infections (typhoid fever, food poisoning) in humans. Salmonellae possess non-specific esterases capable of hydrolyzing chromogenic, for example indigogenic, synthetic substrates or fluorogenic substrates.

The detection/identification of salmonellae, and more generally of microorganisms with esterase activity, is conventionally carried out on gelose or liquid isolating media that allow the detection/identification of suspect colonies of microorganisms with esterase activity, especially salmonellae. The inoculation of such media is effected by immersing said medium in the sample analyzed or by bringing the sample into contact with the medium.

In their enzymatic genotype, microorganisms with esterase activity, particularly salmonellae, possess esterases which cleave the ester linkages of the substrates present in the medium and thus release the activated chromogenic or fluorogenic part of said substrates. This results in a coloration or a fluorescence that reveals hydrolysis and hence the presence of target microorganisms or colonies of target microorganisms.

To be able to perform routine tests on a large scale, it is necessary for the detection/identification media to be stable and to enable the corresponding detection/identification methods to be simplified as far as possible by limiting the manipulations. Also, it is important for the methods to offer a high sensitivity (high intensity of coloration or fluorescence) and a first order specificity. Another fundamental parameter of these types of media and methods for the detection/identification of microorganisms with esterase activity is the rate at which the suspect colonies are revealed.

Now, it is known that esterase substrates present problems of compatibility with culture media for microorganisms with esterase activity. Furthermore, such esterase substrates are not stable over time, meaning that the sensitivity towards esterase activity decreases with storage time.

It would also be valuable to have additives which on the one hand give this kind of medium a translucence in the non-inoculated state (unperturbed growth reading) together with a selectivity towards certain strains, and on the other hand promote the enzymatic activity that is useful as a developer (clearer coloration).

In this context, patent FR 2 697 028 discloses a culture medium for revealing the presence of salmonellae which comprises a chromogenic esterase substrate consisting of an ester of caprylic acid with an indole radical (5-bromo-4-chloro-3-indolyl caprylate), together with a detergent selected from bile salts (sodium deoxycholate). This chromogen and this bile salt are contained in a nutrient medium that allows salmonella to grow. According to the teaching of FR 2 697 028, the bile salt is added directly to the selective medium already containing the esterase substrate.

One disadvantage associated with the use of bile salts derives from the fact that they are starting materials of animal origin, which underlies a certain variability in quality.

In addition, the results in terms of biological activity are capable of improvement.

Furthermore, this culture medium does not offer all the desirable guarantees in terms of stability of the esterase substrate. In fact, the latter proves to be incompletely miscible with the culture medium, which obviously detracts from the quality of the results obtained from the point of view of sensitivity and rapidity.

It must also be noted that the culture medium according to FR 2 697 028 is in the form of a powder. This means that the user first has to carry out an operation to reconstitute the liquid or gelled medium. This constraint is a consequence of the lack of stability of the esterase substrates employed.

In addition, the gelose medium prepared according to the teaching of FR 2 697 028 is not translucent, which is likely to compromise the reading of the colorations associated with any colonies of target bacteria.

Finally, it is indicated on page 3 lines 17-23 of said document that the anionic detergents marketed under the mark Tergitol® by UNION CARBIDE (Na alkylsulfate) do not make it possible to reveal a coloration.

PCT patent application WO-92/17607 relates to a detection medium for salmonellae which contains TERGITOL® 4 (7-ethyl-2-methyl-4-undecanoate hydrogensulfate or its sodium salt). This additive is supposed to improve the selectivity of the detection medium towards germs other than salmonellae (growth inhibition of *Proteus* spp in particular). The concentration of TERGITOL® 4 can vary from 2 to 30 ml/l in the culture medium based on agar gelose/xylose/lysine. According to said document, the detection of salmonellae is based partly on a principle of selective growth by competition. Moreover, this medium does not contain chromogenic or fluorogenic esterase substrates.

PCT patent application WO-99/41409 relates to chromogenic esterase substrates for the detection of salmonellae. Said document proposes the use of a chromogenic compound which reacts with an esterase/lipase specific for the genus *Salmonella* and having an affinity for C8 fatty acid esters. The chromogenic compound in question comprises an anion and a cation of the formula [4-[2-(4-octanoyloxy-3,5-dimethoxyphenyl)vinyl]quinolinium-1-(propan-3-ylcarboxylic acid]$^+$. $^-$[bromide or chloride].

More precisely, the substrates used are C8 esters, for example, of the carboxylate cation. Also, the method according to WO 99/41409 describes the use of a sorbitan fatty acid ester (preferably the sorbitan monolauric acid ester TWEEN® 20). These products are employed as detergents at a rate of 2 g per liter of medium in order to improve the transparency of the medium before inoculation and the coloration of the target colonies for the above-mentioned specific chromogenic esterase substrate. Triton® X100 and Niaproofe® 8 (=Tergitol® 8) are among the detergents cited in said document, along with many other detergents. No example is given of a medium containing Triton® X100 or Niaproof® 8(=Tergitol® 8).

Whatever the case may be, the means disclosed in WO 99/41409 are not presented as providing an improvement in either the selectivity or the specificity of the enzyme substrates contained in the detection medium.

In such a technical environment, one of the essential objectives of the present invention is to provide a medium for the detection/identification of microorganisms with esterase activity which is made up in such a way as to optimize the sensitivity of the analysis, i.e. maximize the intensity of the coloration revealing the presence of target microorganisms (promotion of the esterase activity).

Another essential objective of the present invention is to provide a medium for the detection/identification of microorganisms with esterase activity which is perfectly translucent before inoculation with the sample to be analyzed.

Another essential objective of the invention is to provide a medium for the detection/identification of microorganisms with esterase activity which contains a chromogenic or fluorogenic esterase substrate and is stable on storage (intensity of the revealed colorations maintained at a maximum level for at least several weeks).

Another essential objective of the invention is to provide a medium for the detection/identification of microorganisms with esterase activity which is not in the form of a dry powder that has to be regenerated with a liquid in order to reconstitute a liquid or gelled medium, but which exists directly in ready-to-use forms.

Another essential objective of the invention is to provide a medium for the detection/identification of microorganisms with esterase activity which is economic, especially due to the fact that it comprises reduced amounts of chromogenic or fluorogenic esterase substrate, which is characteristically expensive.

Another essential objective of the invention is to provide a medium for the detection/identification of microorganisms with esterase activity, particularly Gram⁻ enterobacteria, e.g. salmonellae, Gram⁺ bacteria or yeasts.

Another essential objective of the invention is to provide a method of obtaining the above-mentioned detection/identification medium which is simple to carry out and economic.

Another essential objective of the present invention is to provide a method for the detection/identification of strains with esterase activity which is easy to carry out (routine tests), economic (amount of reagent, handling, labor, speed, etc.), reliable, sensitive, specific and reproducible.

These and other objectives are achieved by the present invention, which relates first and foremost to a medium for the detection/identification of microorganisms with esterase activity that is of the type comprising especially a reaction medium (M) (particularly a culture medium) and at least one chromogenic or fluorogenic esterase substrate (S), this detection/identification being based essentially on revealing the presence of the esterase activity, characterized in that:

❖it is in a stable, ready-to-use liquid or gel form; and

❖it contains:

A—at least one solubilizer and stabilizer selected from the group comprising:
 fatty acid sorbitan esters (FASE),
 bile salts, and
 mixtures thereof;

B—at least one selective activator selected from the group comprising:
the compounds of formula (I):

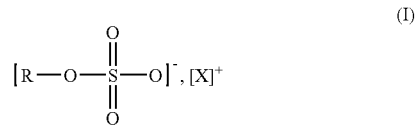

in which:
R is a linear or branched alkyl, preferably C1-C30, and
X is a halogen, preferably Na;
non-ionic polyether derivatives, preferably those of formula (II):

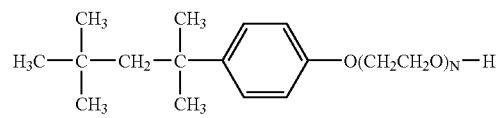

in which:
N is an integer between 2 and 15 (mean =10); and
mixtures thereof; and C—optionally at least one solvent.

The medium according to the invention has the advantage of offering particularly intense colorations of the colonies of target microorganisms with esterase activity. This greatly facilitates the reading and interpretation of the results.

It is also interesting to note that this medium does not favor the growth of microorganisms that do not have esterase activity. This specificity is extremely beneficial for the analysis.

It is also advantageous that this medium is ready to use and is in a liquid or semiliquid (gel) form without presenting a problem in terms of stability. In fact, the esterase substrates present in this medium, even though they are known for their tendency to degrade relatively rapidly, are stabilized through the presence of the additives A, B and optionally C.

These additives bring a further advantage, namely allowing an excellent dissolution of the esterase substrates, which are traditionally reluctant to dissolve. This makes it possible to obtain detection/identification media that are translucent before inoculation, thereby making it easier to read the coloration or fluorescence results.

Finally, these additives A, B and optionally C are relatively inexpensive and make it possible to simplify the procedure and to reduce the amount of esterase substrates used (stabilization), resulting in a definite saving in economic terms.

It is to the inventors' credit to have selected this particular class of specific activators (B) and to have combined them with the solubilizers (A) (e.g. FASE or bile salts). Surprisingly and unexpectedly, they actually afford properties of biological activity, sensitivity, reliability, specificity, stability, selectivity and translucence that are altogether apposite in the microbiological analysis by biochemical means according to the invention.

According to one noteworthy characteristic of the invention, the detection/identification medium to which it relates is obtained by mixing at least one stock solution of the substrate (S) in the solvent (C) with the solubilizer (A), added to at least some of the constituents of the reaction medium (M) and the promoter (B). [sic]

In fact, it appears to be important according to the invention to solubilize the esterase substrate (S) in the solvent (C) in the presence of one or more agents (A). This mixture of substrate (S)/(C)/(A) is then incorporated into at least part of the culture medium (M), which is preferably in a supercooled gelled form. It has been found that this operating characteristic makes it possible to optimize the advantageous results produced by the means according to the invention. The additive (B) is preferably incorporated into the medium afterwards, as explained in detail below.

According to the invention, the selective promoter (B) is a product of formula (I) in which R is a tetradecyl radical (Tergitol® or Niaproof® 4) or a 2-ethylhexyl radical (Tergitol® or Niaproof® 8). The selective promoter (B) can also be a polyethylene glycol mono-p-isooctylphenyl ether of the formula

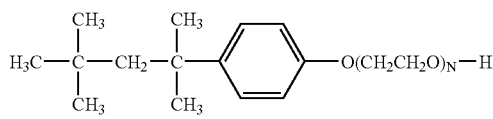

in which:

N is an integer between 2 and 15 (mean=10).

These products are marketed under the marks TRITON X-100®, TRITON X-114® and TRITON X-405®.

Preferably, the FASE (A) is selected from the group comprising:

❖ polyethoxylated sorbitan monolaurate containing 20 units of ethylene oxide (EO)-TWEEN® 20-;

❖ polyethoxylated sorbitan monopalmitate (20 EO)-TWEEN® 40-;

❖ polyethoxylated sorbitan monostearate (20 EO)-TWEEN® 60-;

❖ polyethoxylated sorbitan tristearate (20 EO)-TWEEN® 65-;

❖ polyethoxylated sorbitan monooleate (20 EO)-TWEEN® 80-;

❖ polyethoxylated sorbitan sesquioleate (20 EO)-TWEEN® 83-;

❖ polyethoxylated sorbitan trioleate (20 EO)-TWEEN® 85-; and

❖ mixtures thereof.

The products selected above (sorbitan esters) are widely used in the food and cosmetic industries as non-ionic emulsifiers, but hitherto they have never been employed in microbiological detection/identification media as solubilizers for esterase substrates that are incapable of reacting with lipases and different from the esters of carboxylate salts.

The Hydrophilic-Lipophilic Balances (HLB) of the above-mentioned FASE are respectively 8.6, 6.7, 4.7, 2.1, 4.3, 3.7 and 1.8.

In the case where the target microorganisms are Gram⁺ bacteria and/or yeasts, the concentration of agent (B), expressed in ml per liter of medium (comprising especially A, B, C, M and S), is such that:

$1.10^{-4} \leq [B] \leq 10$, preferably $1.10^{-3} \leq [B] \leq 5$, and particularly preferably $1.10^{-2} \leq [B] \leq 2$.

In the case where the target microorganisms are Gram⁻ bacteria, the concentration of agent (B), expressed in ml per liter of medium (comprising especially A, B, C, M and S), is such that:

$1.10^{-2} \leq [B] \leq 100$, preferably $1.10^{-1} \leq [B] \leq 30$, and particularly preferably $1 \leq [B] \leq 25$.

The use of this synergistic combination (B)/(A)/preferably (C) makes it easier to reveal the presence of the esterase activity in the target microorganisms. It makes it possible to improve the selectivity of the medium and the detection of the esterase activity in esterase⁺ target microorganisms (for example *Salmonella*) without detracting from the expression of other enzymatic activities which might possibly be used to reveal the presence of other target microorganisms in question (β-galactosidase⁺ or β-glucosidase⁺).

Without wishing to be bound by theory, it is assumed that, in this synergistic combination, the compound (B) has an action which favors the penetration of the chromogenic or fluorogenic esterase substrates or the excretion of enzymes across the membranes of the cells of the target microorganisms, for example salmonellae, provided the latter have already been solubilized through the action of (A). This improves the accessibility of these esterase⁺ substrates. Consequently it is possible to reduce the amount of substrates used and derive a definite economic advantage therefrom.

The chromogenic or fluorogenic esterase substrate (S) is advantageously selected from the group comprising:

indoxyl esters of fatty acid(s) and derivatives thereof, preferably indoxyl esters of C6-C11 fatty acid(s) and particularly preferably indoxyl esters of C8-C9 fatty acid(s) that are optionally halogenated;

quinone/anthraquinone esters of fatty acid(s) and derivatives thereof, preferably anthraquinone esters of C6-C11 fatty acid(s) and particularly preferably dihydroxyanthraquinone (alizarin) esters of C8-C9 fatty acid(s);

hydroxycoumarin esters of fatty acid(s) and derivatives thereof;

fluorescein esters of fatty acid(s) and derivatives thereof; and mixtures thereof.

Examples which may be mentioned of chromogenic ester substrates derived from indole are 5-bromo-3-indolyl nonanoate, 6-chloro-3-indolyl nonanoate and 5-bromo-3-indolyl decanoate.

Examples which may be mentioned of chromogenic esterase substrates derived from anthraquinone are alizarin and 2-alizarin octanoate.

The solvent (C) is an auxiliary for solubilizing the chromogenic or fluorogenic esterase substrate. It also complements the action of the solubilizer (A). It is therefore preferably a constituent of the medium according to the invention.

According to an advantageous provision of the invention, the solvent (C) is selected from the group comprising:

alcohols, preferably methanol, ethanol and methoxyethanol;

amides, preferably dimethylformamide (DMF);

sulfur-containing solvents, preferably dimethyl sulfoxide (DMSO); and mixtures thereof.

In practice, the solvents used are methanol, DMF and DMSO.

Even more preferably, the combination (A)=TWEEN® 20, (B)=NIAPROOF® 4 or TERGITOL® 4 and solvent (C)=DMSO seems to be totally effective in the detection/identification medium according to the invention.

It has been found altogether advantageous according to the invention for the proportion by weight of agent (A) to solvent (C) to be between 20:80 and 80:20, preferably between 30:70 and 70:30 and particularly preferably 40:60 or 60:40.

Still from the quantitative point of view, it is preferable for the concentration of agent (A) in the medium to be defined as follows (in % by weight):

✦ $0.1 \leq [A] \leq 10$,

✦ preferably $0.5 \leq [A] \leq 5$,

✦ and particularly preferably $1.5 \leq [A] \leq 3.5$.

The amounts of chromogenic esterase substrate (S) used are such that its concentration in the medium is defined as follows (in mg/l):

✦ $50 \leq [substrate] \leq 1000$,

✦ preferably $100 \leq [substrate] \leq 800$,

✦ and particularly preferably $200 \leq [substrate] \leq 600$.

As regards the culture medium (M) present in the detection/identification medium, it can be specified that it is selected from the group comprising:

selective media of the type comprising MacConkey, Columbia ANC, PALCAM and Sabouraud gentamycin-chloramphenicol media, preferably MacConkey medium; and non-selective media of the type comprising Columbia +/− blood, trypcase soya, nutrient gelose and Sabouraud media, preferably Columbia medium.

In practice, those skilled in the art will choose the culture medium (M) according to the target microorganisms and according to perfectly known criteria with which they are familiar.

Without implying a limitation, it is found that the medium according to the invention is particularly suitable for the detection/identification of bacteria of the genus *Salmonella*. In this case, MacConkey medium, for example, will be chosen as the culture medium.

Furthermore, the medium according to the invention can optionally contain other additives such as one or more other enzyme substrates, for example chromogenic or fluorogenic enzyme substrates, peptones, one or more growth factors, carbohydrates, one or more selective agents, buffers or gelling agents.

The medium according to the invention is in the form of a liquid or gel that is ready to use, i.e. ready for inoculation in a tube or flask or on Petri dishes.

The medium according to the invention can be stored in its containers for several weeks at 4° C. in liquid or gel form.

According to another of its features, the present invention further relates to a method of obtaining the medium as defined above, characterized in that it consists essentially in:

✦ preparing at least one stock solution of the chromogenic or fluorogenic esterase substrate (S) in the solvent (C) and of at least one solubilizer (A), ✦ adding this solution to the culture medium (M), ✦ incorporating the detergent (B) and any other additives into the S+C+A+M mixture, and ✦ homogenizing the whole.

The stock solution is prepared separately by successively incorporating the solvent (C), the substrate (S) and the agent (A), optionally containing co-additives. The products and the amounts used are as defined above.

After homogenization, the stock solution is added to the supercooled gelled culture medium (M) which has been regenerated in water beforehand. The medium can also be a non-gelled liquid medium, for example a nutrient broth.

Mixing of the culture medium (M) and the stock solution gives the liquid or gelled detection medium ready for inoculation.

According to yet another of its features, the invention further relates to a method for the detection/identification of esterase+ strains (for example salmonellae) which consists in:

inoculating the detection/identification medium as defined above, either as a product per se or as a product obtained by the method also described above, with the sample suspected of containing the microorganisms to be analyzed;

incubating the inoculated medium under appropriate conditions known to those skilled in the art; and reading/interpreting the colorations or fluorescences of the colonies which have developed after incubation, for example in an oven at 37° C., these colorations or fluorescences revealing hydrolysis of the chromo-genic or fluorogenic esterase substrate by the target microorganisms.

Finally, the invention further relates to the use, as a selective activator, of at least one product (B) selected from the group comprising:

the compounds of formula (I):

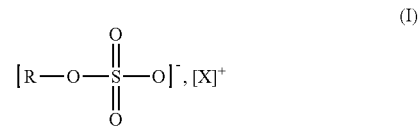

in which:

R is a linear or branched alkyl, preferably C1-C30, and

X is a halogen, preferably Na;

non-ionic polyether derivatives, preferably those of formula (II):

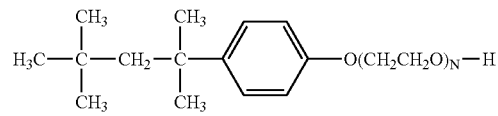

in which:

N is an integer between 2 and 15 (mean=10); and mixtures thereof.

The Examples which follow will provide a clearer understanding of the invention and make it possible to assess all its advantages as well as its diverse embodiments and modes of implementation.

EXAMPLES

Example 1

Use of Tergitol 4 in a Gelled Medium Containing a Chromogenic Esterase Substrate for Improving the Expression of the Esterase Activity in Gram-Negative Bacterial Species Exhibiting this Activity The esterase substrate tested is 5-bromo-3-indolyl nonanoate. A 40 g/l stock solution of substrate is prepared in a mixture of 40% dimethyl sulfoxide and 60% Tween 20. A sufficient volume is added to a supercooled MacConkey medium (without neutral red) to give a substrate concentration of 500 mg/l.

This medium is then separated into five portions and a defined concentration of Tergitol 4 is added to each one (cf. Table below). Microorganisms originating from the Applicant's collection were inoculated onto this medium from a 0.5 McFarland suspension by isolation in three quadrants. The dishes were incubated at 37° C. for 48 hours. The colonies formed were examined visually after 24 and 48 hours of incubation. The coloration of these colonies and the intensity of this coloration were noted. The results are shown in Table 1 below:

exhibiting an esterase activity. The most effective concentration depends on the strain and also on the desired effect. For certain strains it even seems possible to increase this concentration further.

Example 2

Use of Tergitol 4 in a Gelled Medium Containing an Indoxyl-Based Esterase Substrate Dissolved in a Mixture of DMSO and Bile Salts The esterase substrate tested is 5-bromo-3-indolyl nonanoate. A 25 g/l stock solution of substrate is prepared in methanol to which 5 g/l of bile salts have been added. A sufficient volume is added to a supercooled MacConkey medium (without neutral red) to give a substrate concentration of 500 mg/l.

This medium is then separated into five portions and a defined concentration of Tergitol 4 is added to each one (cf. Table below). Microorganisms originating from the Applicant's collection were inoculated onto this medium from a 0.5 McFarland suspension by isolation in three quadrants. The dishes were incubated at 37° C. for 48 hours. The colonies formed were examined visually after 24 and 48

TABLE 1

| Strain | Medium IT | without Tergitol 4 | | with 2 ml/l of Tergitol 4 | | with 4 ml/l of Tergitol 4 | | with 8 ml/l of Tergitol 4 | | with 16 ml/l of Tergitol 4 | |
|---|---|---|---|---|---|---|---|---|---|---|---|
| | | C | I | C | I | C | I | C | I | C | I |
| Salmonella spp. | 24 h | gray | 1 | gray | 1 | gray | 1.5 | gray | 2 | gray | 1 |
| 017 | 48 h | gray | 2 | gray | 3 | gray | 3.5 | gray | 3 | gray | 2 |
| Salmonella typhimurium | 24 h | gray | 2 | gray | 2 | gray | 3 | gray | 3.5 | gray | 3.5 |
| 010 | 48 h | gray | 2 | gray | 2.5 | gray | 3 | gray | 3.5 | gray | 4 |
| Salmonella enteritidis | 24 h | gray | 2 | gray | 2 | gray | 3 | gray | 3.5 | gray | 3.5 |
| 002 | 48 h | gray | 2 | gray | 2 | gray | 3 | gray | 3.5 | gray | 3.5 |
| Salmonella paratyphi A | 24 h | gray | 2 | gray | 2 | gray | 2 | gray | 3 | gray | 2 |
| 006 | 48 h | gray | 2 | gray | 2 | gray | 2.5 | gray | 3 | gray | 2 |
| Salmonella typhi | 24 h | gray | 2 | gray | 2 | gray | 2 | gray | 3 | gray | 3 |
| 118 | 48 h | gray | 2 | gray | 2 | gray | 3 | gray | 3.5 | gray | 3.5 |
| Salmonella arizonae | 24 h | gray | 2 | gray | 2 | gray | 3.5 | gray | 3.5 | gray | 3.5 |
| 018 | 48 h | gray | 2.5 | gray | 2.5 | gray | 3.5 | gray | 3.5 | gray | 4 |
| Escherichia coli | 24 h | — | — | — | — | — | — | — | — | — | — |
| 002 | 48 h | — | — | — | — | — | — | — | — | — | — |
| Hafnia alvei | 24 h | — | — | — | — | — | — | — | — | — | — |
| 025 | 48 h | — | — | — | — | — | — | — | — | — | — |
| Enterobacter cloacae | 24 h | gray | 0.5 | gray | 0.5 | gray | 1 | gray | 0.5 | gray | 0.5 |
| 086 | 48 h | gray | 1.5 | gray | 2 | gray | 3 | gray | 1 | gray | 1 |
| Serratia marcescens | 24 h | gray | 3 | gray | 2 | gray | 2 | gray | 2 | gray | 2 |
| 038 | 48 h | gray | 3.5 | gray | 3 | gray | 4 | gray | 4 | gray | 4 |
| Pseudomonas aeruginosa | 24 h | gray | 3 | gray | 3.5 | gray | 4 | gray | 4 | gray | 4 |
| 165 | 48 h | gray | 3 | gray | 3.5 | gray | 4 | gray | 4 | gray | 4 |
| Acinetobacter calcoaceticus | 24 h | gray | 2 | gray | 2 | gray | 3 | gray | 3 | gray | 0.5 |
| 034 | 48 h | gray | 3 | gray | 3 | gray | 3 | gray | 4 | gray | 0.5 |

—: absence of color or intensity;
IT: incubation time; intensity of coloration: arbitrary scale At a concentration of between 2 and 16 ml/l and more precisely of between 4 and 8 ml/l, Tergitol 4 significantly increases the intensity of coloration of bacterial strains hours of incubation. The coloration of these colonies and the intensity of this coloration were noted. The results are shown in Table 2 below:

TABLE 2

| Strain | Medium IT | without Tergitol 4 C | I | with 2 ml/l of Tergitol 4 C | I | with 4 ml/l of Tergitol 4 C | I | with 8 ml/l of Tergitol 4 C | I | with 16 ml/l of Tergitol 4 C | I |
|---|---|---|---|---|---|---|---|---|---|---|---|
| *Salmonella* spp. | 24 h | — | — | gray | 1 | gray | 1 | gray | 1 | gray | 1 |
| 017 | 48 h | gray | 1 | gray | 1.5 | gray | 1.5 | gray | 1.5 | gray | 1.5 |
| *Salmonella typhimurium* | 24 h | gray | 0.5 | gray | 2 | gray | 2 | gray | 3 | gray | 3 |
| 010 | 48 h | gray | 1 | gray | 2 | gray | 3 | gray | 3 | gray | 3.5 |
| *Salmonella enteritidis* | 24 h | gray | 0.5 | gray | 2 | gray | 3 | gray | 0.5 | gray | 0.1 |
| 002 | 48 h | gray | 1 | gray | 3 | gray | 3 | gray | 2 | gray | 1 |
| *Salmonella paratyphi* A | 24 h | — | — | gray | 0.1 | gray | 0.1 | — | — | — | — |
| 006 | 48 h | gray | 0.5 | gray | 0.5 | gray | 1 | — | — | — | — |
| *Salmonella typhi* | 24 h | — | — | — | — | — | — | — | — | — | — |
| 118 | 48 h | — | — | — | — | — | — | — | — | — | — |
| *Salmonella arizonae* | 24 h | gray | 0.5 | gray | 2.5 | gray | 2 | gray | 0.5 | gray | 0.5 |
| 018 | 48 h | gray | 1.5 | gray | 3 | gray | 2.5 | gray | 1.5 | gray | 2 |
| *Escherichia coli* | 24 h | — | — | — | — | — | — | — | — | — | — |
| 002 | 48 h | — | — | — | — | — | — | — | — | — | — |
| *Hafnia alvei* | 24 h | — | — | — | — | — | — | — | — | — | — |
| 025 | 48 h | — | — | — | — | — | — | — | — | — | — |
| *Enterobacter cloacae* | 24 h | gray | 0.5 | gray | 0.5 | gray | 1 | gray | 0.5 | gray | 0.5 |
| 086 | 48 h | gray | 1.5 | gray | 2 | gray | 3 | gray | 1 | gray | 1 |
| *Serratia marcescens* | 24 h | gray | 1 | gray | 2 | gray | 2 | gray | 2 | gray | 2 |
| 038 | 48 h | gray | 1.5 | gray | 3 | gray | 4 | gray | 4 | gray | 4 |
| *Pseudomonas aeruginosa* | 24 h | gray | 1 | gray | 3.5 | gray | 4 | gray | 4 | gray | 4 |
| 165 | 48 h | gray | 1.5 | gray | 3.5 | gray | 4 | gray | 4 | gray | 4 |
| *Acinetobacter calcoaceticus* | 24 h | gray | 2 | gray | 2 | gray | 3 | gray | 3 | gray | 0.5 |
| 034 | 48 h | gray | 3 | gray | 3 | gray | 3 | gray | 4 | gray | 0.5 |

—: absence of color or intensity;
IT: incubation time;
C: color;
I: intensity; intensity of coloration: arbitrary scale At a concentration of between 2 and 16 ml/l and more precisely of between 4 and 8 ml/l, Tergitol 4 significantly increases the intensity of coloration of bacterial strains exhibiting an esterase activity. The most effective concentration depends on the strain. These results clearly show that the effect of Tergitol 4 on the esterase activity does not depend on the mode of use of the substrate.

Example 3

Use of Tergitol 4 in a Gelled Medium Containing a Chromogenic Esterase Substrate for Improving the Expression of the Esterase Activity in Gram-Positive Bacterial Species and Yeasts Exhibiting this Activity The esterase substrate tested is 5-bromo-4-chloro-3-indolyl nonanoate. A 40 g/l stock solution of substrate is prepared in a mixture of 40% dimethyl sulfoxide and 60% Tween 20. A sufficient volume is added to a supercooled MacConkey medium (without neutral red) to give a substrate concentration of 250 mg/l.

This medium is then separated into six portions and a defined concentration of Tergitol 4 is added to each one (cf. Table below). Microorganisms originating from the Applicant's collection were inoculated onto this medium from a 0.5 McFarland suspension by isolation in three quadrants. The dishes were incubated at 37° C. for 48 hours. The colonies formed were examined visually after 24 and 48 hours of incubation. The coloration of these colonies and the intensity of this coloration were noted. The results are shown in Table 3 below:

TABLE 3

| Strain | Medium IT | without Tergitol 4 C | I | with 0.001 ml/l of Tergitol 4 C | I | with 0.01 ml/l of Tergitol 4 C | I | with 0.1 ml/l of Tergitol 4 C | I | with 1 ml/l of Tergitol 4 C | I | with 1 ml/l of Tergitol 4 C | I |
|---|---|---|---|---|---|---|---|---|---|---|---|---|---|
| *Listeria monocytogenes* | 24 h | T | 2 | T | 2 | T | 2.5 | T | 2 | T | 2 | T | 2 |
| 023 | 48 h | T | 2 | T | 2 | T | 3 | T | 3 | T | 3 | T | 3 |
| *Listeria monocytogenes* | 24 h | T | 2 | T | 2 | T | 3 | T | 2 | T | 2 | T | 2 |
| 079 | 48 h | T | 3 | T | 3 | T | 3 | T | 3 | T | 3 | T | 3 |
| *Listeria innocua* | 24 h | T | 0.1 | T | 0.1 | T | 0.1 | T | 0.1 | T | 0.1 | T | 0.1 |
| 029 | 48 h | T | 2 | T | 2 | T | 2 | T | 2 | T | 2 | T | 2 |

TABLE 3-continued

| Strain | Medium IT | without Tergitol 4 | | with 0.001 ml/l of Tergitol 4 | | with 0.01 ml/l of Tergitol 4 | | with 0.1 ml/l of Tergitol 4 | | with 1 ml/l of Tergitol 4 | | with 1 ml/l of Tergitol 4 | |
|---|---|---|---|---|---|---|---|---|---|---|---|---|---|
| | | C | I | C | I | C | I | C | I | C | I | C | I |
| Staphylococcus aureus | 24 h | T | 1 | T | 2 | T | 2 | T | 3 | T | 2 | T | 2 |
| 276 | 48 h | T | 3 | T | 2 | T | 3 | T | 3 | T | 3 | T | 3 |
| Staphylococcus epidermidis | 24 h | T | 2 | T | 2 | T | 3 | T | 2 | T | 2 | T | 0.5 |
| 009 | 48 h | T | 2 | T | 2 | T | 3 | T | 3 | T | 2 | T | 3 |
| Salmonella spp. | 24 h | T | 2 | T | 2 | T | 2 | T | 2 | T | 2 | T | 2 |
| 017 | 48 h | T | 3 | T | 3 | T | 3 | T | 3 | T | 3 | T | 3 |
| Salmonella paratyphi A | 24 h | T | 0.1 | T | 0.1 | T | 0.1 | T | 0.1 | T | 0.5 | T | 0.5 |
| 006 | 48 h | T | 0.5 | T | 0.5 | T | 1 | T | 0.5 | T | 2 | T | 2 |
| Pseudomonas aeruginosa | 24 h | T | 0.1 | T | 0.1 | T | 0.5 | T | 0.1 | T | 0.5 | T | 0.5 |
| 165 | 48 h | T | 0.5 | T | 0.5 | T | 1 | T | 0.5 | T | 0.5 | T | 1 |
| Candida albicans | 24 h | T | 0.1 | T | 0.5 | T | 0.5 | T | 0.5 | T | 0.5 | T | 0.5 |
| 033 | 48 h | T | 2.5 | T | 3 | T | 3 | T | 3 | T | 3 | T | 3 |
| Candida tropicalis | 24 h | T | 0.5 | T | 2 | T | 2 | T | 2 | T | 0.5 | T | 0.5 |
| 030 | 48 h | T | 3 | T | 3 | T | 3 | T | 3 | T | 3 | T | 3 |

—: absence of color or intensity;
IT: incubation time; intensity of coloration: arbitrary scale The choice of Tergitol 4 concentrations well below those tested in the previous Examples was dictated by the type of strain tested. In fact, they are either Gram-positive bacteria or yeasts; now, at excessive Tergitol 4 concentrations, this type of strain cannot develop on a culture medium.

In the same way as in the previous Examples, it is possible to observe a positive effect of Tergitol 4 on the expression of the esterase activity in the microorganisms tested. This effect varies from one bacterial species to another. The choice of a Tergitol 4 concentration also depends on the species. In general, the effective concentrations for Gram-positive bacteria and yeasts are well below those used for Gram-negative bacteria. However, at the concentrations tested, it is possible to observe a slight positive impact on the coloration of the Gram-negative bacteria tested in this Example.

Example 4

Use of Two Other Surfactants, Tergitol 8 and Triton X100 (Non-Ionic Surfactant), in a Gelled Medium Containing a Chromogenic Esterase Substrate for Improving the Expression of the Esterase Activity in Bacterial Species Exhibiting this Activity The esterase substrate tested is 5-bromo-3-indolyl nonanoate. A 40 g/l stock solution of substrate is prepared in a mixture of 40% dimethyl sulfoxide and 60% Tween 20. A sufficient volume is added to a supercooled MacConkey medium (without neutral red) to give a substrate concentration of 500 mg/l.

This medium is then separated into eight portions. The first portion is transferred directly to Petri dishes, 8 ml/l of Tergitol 4 are added to the second portion, Tergitol 8 at concentrations of 2, 4 and 8 ml/l is added to the next three and, finally, the last three contain Triton X100 at concentrations of 8, 16 and 32 m/l. Microorganisms originating from the Applicant's collection were inoculated onto this medium from a 0.5 McFarland suspension by isolation in three quadrants. The dishes were incubated at 37° C. for 48 hours. The colonies formed were examined visually after 24 and 48 hours of incubation. The coloration of these colonies and the intensity of this coloration were noted. The results are shown in Tables 4 and 5 below:

TABLE 4

| Strain | Medium IT | without Tergitol 4 | | with 8 ml/l of Tergitol 4 | | with 2 ml/l of Tergitol 8 | | with 4 ml/l of Tergitol 8 | | with 8 ml/l of Tergitol 8 | |
|---|---|---|---|---|---|---|---|---|---|---|---|
| | | C | I | C | I | C | I | C | I | C | I |
| Salmonella | 24 h | gray | 1 | gray | 2.5 | gray | 0.5 | gray | 0.3 | — | — |
| spp. 017 | 48 h | gray | 2 | gray | 3.5 | gray | 1.5 | gray | 1 | gray | 0.5 |
| Salmonella | 24 h | gray | 2 | gray | 3 | gray | 3 | gray | 2.5 | gray | 3 |
| enteritidis 006 | 48 h | gray | 2 | gray | 3 | gray | 4 | gray | 3 | gray | 3.5 |
| Salmonella | 24 h | gray | 2 | gray | 3 | gray | 1.5 | gray | 1 | gray | 1 |
| typhi 118 | 48 h | gray | 2 | gray | 3.5 | gray | 2 | gray | 1.5 | gray | 1 |
| Salmonella | 24 h | gray | 2 | gray | 3.5 | gray | 2 | gray | 2 | gray | 2 |
| arizonae 018 | 48 h | gray | 2.5 | gray | 3.5 | gray | 4 | gray | 2.5 | gray | 2.5 |
| Escherichia | 24 h | — | — | — | — | — | — | — | — | — | — |
| coli 002 | 48 h | — | — | — | — | — | — | — | — | — | — |

TABLE 4-continued

| | Medium | without Tergitol 4 | | with 8 ml/l of Tergitol 4 | | with 2 ml/l of Tergitol 8 | | with 4 ml/l of Tergitol 8 | | with 8 ml/l of Tergitol 8 | |
|---|---|---|---|---|---|---|---|---|---|---|---|
| Strain | IT | C | I | C | I | C | I | C | I | C | I |
| *Hafnia alvei* 025 | 24 h | — | — | — | — | — | — | — | — | — | — |
| | 48 h | — | — | — | — | — | — | — | — | — | — |

TABLE 5

| | Medium | without Tergitol 4 | | with 8 ml/l of Tergitol 4 | | with 8 ml/l of Triton X100 | | with 16 ml/l of Triton X100 | | with 32 ml/l of Triton X100 | |
|---|---|---|---|---|---|---|---|---|---|---|---|
| Strain | IT | C | I | C | I | C | I | C | I | C | I |
| *Salmonella* spp. 017 | 24 h | gray | 1 | gray | 2.5 | gray | 1 | gray | 0.5 | — | — |
| | 48 h | gray | 2 | gray | 3.5 | gray | 3 | gray | 2 | gray | 0.5 |
| *Salmonella enteritidis* 006 | 24 h | gray | 2 | gray | 3 | gray | 2 | gray | 2 | gray | 1 |
| | 48 h | gray | 2 | gray | 3 | gray | 2.5 | gray | 2.5 | gray | 1.5 |
| *Salmonella typhi* 118 | 24 h | gray | 2 | gray | 3 | gray | 1 | gray | 1 | gray | 0.5 |
| | 48 h | gray | 2 | gray | 3.5 | gray | 1 | gray | 1 | gray | 0.5 |
| *Salmonella arizonae* 018 | 24 h | gray | 2 | gray | 3.5 | gray | 2 | gray | 2 | gray | 1 |
| | 48 h | gray | 2.5 | gray | 3.5 | gray | 2.5 | gray | 2.5 | gray | 2 |
| *Escherichia coli* 002 | 24 h | — | — | — | — | — | — | — | — | — | — |
| | 48 h | — | — | — | — | — | — | — | — | — | — |
| *Hafnia alvei* 025 | 24 h | — | — | — | — | — | — | — | — | — | — |
| | 48 h | — | — | — | — | — | — | — | — | — | — |

—: absence of colour or intensity;
IT: incubation time;
C: color;
I intensity; intensity of coloration: arbitrary scale Different concentration ranges were tested beforehand in order to study the effect of these compounds on bacterial growth. The most interesting points were then singled out for this Example.

Under the experimental conditions tested, the effect obtained with Tergitol 8 and Triton X100 on the esterase activity is not as pronounced as that observed with Tergitol 4.

Note: In the above Examples, the numbers following the strains correspond to the number of each strain referenced in the Applicant's collection. The intensity of coloration corresponds to an arbitrary scale defined as follows:

| 0 | no activity |
|---|---|
| 0.1 | trace of coloration |
| 0.5 | very pale coloration |
| 1 | distinct coloration of low intensity |
| 2 | clear coloration of medium intensity |
| 3 | intense coloration |
| 4 | very intense coloration |

The invention claimed is:

1. A medium for the detection/identification of microorganisms with esterase activity comprising a reaction medium (M) and at least one chromogenic or fluorogenic esterase substrate (S), this detection/identification being based essentially on revealing the presence of the esterase activity, wherein the improvement consists in that:
the medium for the detection/identification of microorganisms with esterase activity is in a stable, ready-to-use liquid or gel form; and
the medium for the detection/identification of microorganisms with esterase activity contains:
—A—at least one solubilizer and stabilizer selected from the group consisting of:
fatty acid sorbitan esters (FASE),
and mixtures of FASE and bile salts;
—B—a selective activator of formula (I);

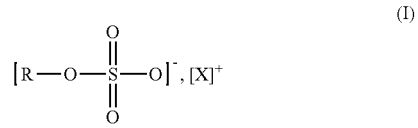

in which:
R is a tetradecyl, and
x is Na;
—C—optionally at least one solvent.

2. The medium according to claim 1, obtained by mixing at least one stock solution of the substrate (S) and the solvent (C) with the solubilizer (A), added to at least some of the constituents of the reaction medium (M) and the selective activator (B).

3. The medium according to claim 1, wherein the FASE (A) is selected from the group consisting of:
polyethoxylated sorbitan monolaurate containing 20 units of ethylene oxide;
polyethoxylared sorbitan monopalminate containing 20 units of ethylene oxide;
polyethoxylated sorbitan monostearate containing 20 units of ethylene oxide;

polyethoxylated sorbitan tristearate containing 20 units of ethylene oxide;

polyethoxylated sorbitan monooleate containing 20 units of ethylene oxide;

polyethoxylated sorbitan sesquioleate containing 20 units of ethylene oxide;

polyethoxylaxed sorbitan trioleate containing 20 units of ethylene oxide; and mixtures thereof.

4. The medium according to claim 1, wherein the target micro-organisms are Gram$^+$ bacteria and/or yeasts and wherein the concentration of selective activator (B), expressed in ml per liter of medium, is such that: $1 \times 10^{-4} \leq [B] \leq 10$.

5. The medium according to claim 1, wherein the target micro-organisms are Gram$^-$ bacteria and wherein the concentration of selective activator (B), expressed in ml per liter of medium is such that: $1 \times 10^{-2} \leq [B] \leq 100$.

6. The medium according to claim 1, wherein the chromogenic or fluorogenic esterase substrate is selected from the group consisting of:

indoxyl esters of fatty acid(s) and derivatives thereof;

quinone/anthraquinone esters of fatty acid(s) and derivatives thereof;

hydroxycoumarin esters of fatty acid(s) and derivatives thereof;

fluorescein esters of fatty acids and derivatives thereof; and mixtures thereof.

7. The medium according to claim 1, wherein the solvent (C) is selected from the group consisting of:

alcohols;

amides, sulfur-containing solvents; and mixtures thereof.

8. The medium according to claim 1, wherein the proportion by weight of solubilizer and stabilizer (A) to solvent (C) is between 20:80 and 80:20.

9. The medium according to claim 1, wherein the concentration of solubilizer and stabilizer (A) in the medium is defined as follows (in % by weight): $0.1 \leq [A] \leq 10$.

10. The medium according to claim 1, wherein the concentration of substrate (S) in the medium is defined as follows (in mg/l): $50 \leq [S] \leq 1000$.

11. The medium according to claim 1, wherein the culture medium (M) is selected from the group consisting of:

selective media selected from the type comprising MacConkey, Columbia ANC, PALCAM and Sabouraud gentamycin-chloramphenicol media; and non-selective media of the type comprising Columbia +/− blood, trypcase soy; nutrient gelose and Sabouraud media.

12. The medium according to claim 1, wherein the bacteria to be detected/identified are salmonellae.

13. The method of obtaining the medium according to claim 1, consisting essentially of:

preparing at least one stock solution of the chromogenic or fluorogenic esterase substrate (S) and of at least one solubilizer (A) in the solvent (C), adding this solution to the reaction medium (M), incorporating the selective activator (B) and any other additives into the S+A+C+M mixture, and homogenizing the whole.

14. The method for the detection/identification of strains with esterase activity, consisting of:

inoculating the medium according to claim 1, with a sample suspected of containing the microorganisms to be analyzed or detected/identified, incubating the inoculated medium under appropriate conditions, and reading and interpreting the colorations or fluorescences of the colonies, these colorations or fluorescence, revealing hydrolysis of the substrate by the target microorganisms.

15. The medium according to claim 4, wherein the concentration of selective activator (B), expressed in ml per liter of medium, is such that: $1 \times 10^{-3} \leq [B] \leq 5$.

16. The medium according to claim 4, wherein the concentration of selective activator (B), expressed in ml per liter of medium, is such that: $1 \times 10^{-2} \leq [B] \leq 2$.

17. The medium according to claim 5, wherein the concentration of selective activator (B), expressed in ml per liter of medium, is such that: $1 \times 10^{-1} \leq [B] \leq 30$.

18. The medium according to claim 5, wherein the concentration of selective activator (B), expressed in ml per liter of medium, is such that: $1 \leq [B] \leq 25$.

19. The medium according to claim 6, wherein the indoxyl ester(s) of taffy acid(s) are selected from the group consisting of indoxyl esters of C6-C11 fatty acid(s) and halogenated indoxyl esters of C6-C11 fatty acid(s).

20. The medium according to claim 6, wherein the indoxyl ester(s) of fatty acid(s) are selected from the group consisting of indoxyl esters of C8-C9 fatty acid(s) and halogenated indoxyl esters of C8-C9 fatty acid(s).

21. The medium according to claim 6, wherein quinone/anthraquinone esters of fatty acid(s) are anthraquinone esters of C6-C11 fatty acid(s).

22. The medium according to claim 6, wherein quinone/anthraquinone esters of fatty acid(s) and derivatives thereof are dihydroxyanthraquinone (alizarin) esters of C8-C9 fatty acid(s).

23. The medium according to claim 7, wherein the solvent (C) is an alcohol selected from the group consisting of methanol, ethanol and methoxyethanol.

24. The medium according to claim 7, wherein the solvent (C) is an amide which is dimethylformamide (DMF).

25. The medium according to claim 7 wherein the solvent (C) is sulphur containing solvent which is dimethyl sulfoxide (DMSO).

26. The medium according to claim 8, wherein the proportion by weight of solubilizer (A) to solvent (C) is between 30:70 and 70:30.

27. The medium according to claim 8, wherein the proportion by weight of solubilizer (A) to solvent (C) is between 40:60 or 60:40.

28. The medium according to claim 9, wherein the concentration of solubilizer and stabilizer (A) in the medium is defined as follows (in % by weight): $0.5 \leq [A] 5$.

29. The medium according to claim 9, wherein the concentration of solubilizer and stabilizer (A) in the medium is defined as follows (in % by weight): $1.5 \leq [A] \leq 3.5$.

30. The medium according to claim 10, wherein the concentration of substrate (S) in the medium is defined as follows (in mg/l): $100 \leq [S] \leq 800$.

31. The medium according to claim 10, wherein the concentration of substrate (S) in the medium is defined as follows (in mg/l): $200 \leq [S] \leq 600$.

32. The medium according to claim 11, wherein the culture medium (M) is selected from the group consisting of MacConkey medium or Columbia medium.

* * * * *